(12) United States Patent
Coghill (10) Patent No.: US 7,856,881 B2
(45) Date of Patent: Dec. 28, 2010

(54) DETERMINING AVERAGE MECHANICAL PROPERTIES OF CONSTITUENT PARTICLES OF A SAMPLE OF MATERIAL USING ULTRASOUND

(75) Inventor: Peter Coghill, New South Wales (AU)

(73) Assignee: Commonwealth Scientific and Industrial Research Organisation, Campbell (AU)

( * ) Notice: Subject to any disclaimer, the term of this patent is extended or adjusted under 35 U.S.C. 154(b) by 580 days.

(21) Appl. No.: 11/886,838

(22) PCT Filed: Mar. 21, 2006

(86) PCT No.: PCT/AU2006/000375
§ 371 (c)(1),
(2), (4) Date: Sep. 21, 2007

(87) PCT Pub. No.: WO2006/099666
PCT Pub. Date: Sep. 28, 2006

(65) Prior Publication Data
US 2009/0078046 A1    Mar. 26, 2009

(30) Foreign Application Priority Data
Mar. 22, 2005  (AU) .............................. 2005901409

(51) Int. Cl.
*G01H 5/00* (2006.01)
(52) U.S. Cl. .......................................... 73/597; 73/602
(58) Field of Classification Search .................. 73/597, 73/570, 584, 587, 596, 602, 618, 620, 627, 73/628, 649
See application file for complete search history.

(56) References Cited

U.S. PATENT DOCUMENTS

| | | | | | |
|---|---|---|---|---|---|
| 3,779,070 | A | * | 12/1973 | Cushman et al. | 73/865.5 |
| 4,202,215 | A | * | 5/1980 | Meyer | 73/599 |
| 4,414,850 | A | * | 11/1983 | Miwa et al. | 73/599 |
| 4,509,524 | A | * | 4/1985 | Miwa | 600/442 |
| 4,594,896 | A | * | 6/1986 | Cardoso et al. | 73/599 |
| 4,688,428 | A | * | 8/1987 | Nicolas | 73/602 |
| 4,750,366 | A | * | 6/1988 | Nicolas | 73/602 |

(Continued)

FOREIGN PATENT DOCUMENTS

JP    09-281092    10/1997

(Continued)

OTHER PUBLICATIONS

Fukuda et al. (English Translation of Japanese Patent Application Publication JP 09-281092).*

(Continued)

*Primary Examiner*—Hezron Williams
*Assistant Examiner*—Samir M Shah
(74) *Attorney, Agent, or Firm*—Nixon & Vanderhye P.C.

(57) ABSTRACT

The average strength or Young's modulus of the constituent particles of a sample is determined from the measured speed of sound propagated from a source through the sample to a receiver. Other sample data, such as the porosity, Poisson's ratio and the pressure applied to the sample, are also used in the determination. However, no data pertaining to individual particle sizes is required. The method provides a non-destructive test for the average strengths of materials such as iron ore pellets, alumina powder, silica flour, and coal dust.

33 Claims, 5 Drawing Sheets

U.S. PATENT DOCUMENTS

| | | | |
|---|---|---|---|
| 5,952,560 A * | 9/1999 | Collings et al. | 73/61.75 |
| 6,487,894 B1 * | 12/2002 | Dukhin et al. | 73/61.75 |
| 6,604,408 B2 * | 8/2003 | Dosramos et al. | 73/61.75 |
| 7,383,730 B2 * | 6/2008 | Huang et al. | 73/597 |
| 2006/0178581 A1 * | 8/2006 | Africk et al. | 600/440 |
| 2006/0219012 A1 * | 10/2006 | Huang et al. | 73/597 |

FOREIGN PATENT DOCUMENTS

WO  99/01727  1/1999

OTHER PUBLICATIONS

International Search Report for PCT/AU2006/000375 mailed Jun. 1, 2006.
Demand (PCT/IPEA/401) published Jan. 1, 2007.
International Preliminary Report on Patentability (PCT/IPEA/409) completed Jan. 5, 2007.
Written Opinion (PCT/ISA/237) mailed Jun. 1, 2006.
Response to Written Opinion dated Nov. 24, 2006.
P. J. Digby, "The Effective Elastic Moduli of Porous Granular Rocks"; Journal of Applied Mechanics; Dec. 1981; vol. 48; pp. 803-808.

* cited by examiner

DETERMINING AVERAGE MECHANICAL PROPERTIES OF CONSTITUENT PARTICLES OF A SAMPLE OF MATERIAL USING ULTRASOUND

This application is the U.S. national phase of International Application No. PCT/AU2006/000375 filed 21 Mar. 2006 which designated the U.S. and claims priority to AU 2005901409 filed 22 Mar. 2005, the entire contents of each of which are hereby incorporated herein by reference.

FIELD OF THE INVENTION

This invention relates to a system for, and a method of, determining average mechanical properties of constituent particles of a sample of material using ultrasound.

BACKGROUND TO THE INVENTION

In many industries it is desirable to determine properties of constituent particles of a sample of material. Such materials include powders, and aggregates such as granules, pellets and briquettes. One property of interest is the strength of constituent particles of a sample of material.

For instance, certain industries produce aggregates as finished or intermediate products and the strength of the aggregated product is important to the marketability of the product as breakdown of the product defeats the purpose of the aggregation operation. In the iron ore industry, aggregates in the form of pellets are individually tested for strength by controlled crushing. However such a technique is time consuming as the process occurs on a pellet by pellet basis. Furthermore, the technique is destructive as pellets are generally destroyed in the process. It is desirable to rapidly determine the average strength of the pellets, in bulk using a non destructive technique.

A further property of interest is the dusting characteristics of powders which is directly related to the strength of the particulates which make up the powder. Insufficient particulate strength leads to dusting, which may interfere with production line processing as clogged machinery will lead to a temporary shut down of the plant.

In the alumina industry, alumina powder is produced by the process of crystallisation and calcination. In order to test the strength of the particulates making up the calcined powder, a sample of the calcined powder is typically subject to an attrition test. This test involves mechanically shaking the sample and making successive measurements to determine the change in size of the individual particles. From this the strength is able to be calculated. Again, measurements on individual particles is time consuming. Furthermore, the measurement is performed on the calcined product. It is desirable to be able to determine the average properties of particulates of the material in bulk and prior to calcination.

Aggregates are also produced in many non-mineral industries such as food production and laundry detergent, powder manufacture. Thus, a wide variety of products are produced as aggregates in respect of which it may be desirable to determine material properties.

SUMMARY OF THE INVENTION

According to a first aspect of the invention, there is provided a method of determining average properties of constituent particles of a sample of material, the method including:

transmitting sound waves through the sample;

receiving a sound signal representative of sound waves transmitted through the sample;

providing reference data regarding selected criteria associated with the sample; and processing the received signal and using the reference data to determine, independently of particle size of particles constituting the sample, predetermined average properties of the particles constituting the sample.

The material may be a powder. The material may be an aggregate, such as, but not limited to, granules, pellets or briquettes.

Preferably, the method includes determining particle strength based on measured sound velocity independently of particle size. More particularly, the method may include calculating the Young's modulus of the particles, and from this calculation determining the particle strength.

The Young's modulus of the particles may be obtained from an equation derived from a random packing order of spheres:

$$V = 0.392 V_b \left( K^{1/3} \left( \frac{1}{1-\nu} \right)^{1/3} \left( \frac{1}{1-\alpha} \right)^{1/6} \left( \frac{P}{E} \right)^{1/6} \right) \text{ where:}$$

V is the sound velocity of the wave injected into the sample of material, $V_b$ is the sound velocity of the wave having propagated through the sample of material, K is the average number of contacts for each sphere, which for a random packing is 8.84, α is the voidage fraction, ν is Poisson's ratio of the individual particles in the sample of material, P is the applied pressure, and E is the Young's modulus.

From the above equation, it will be noted that the sound velocity is proportional to 0.167 the power of the pressure applied.

Preferably the method includes applying a pressure to the sample to facilitate sound transmission. The pressure applied to the sample may be of the order of $10^{-6}$ of the Young's modulus of particles of the sample. The method may further comprise measuring the pressure applied to the sample.

The method may further comprise measuring a bulk density of the sample.

The method may further comprise selecting a frequency of the sound waves for transmission through the sample, where the frequencies are selected within a range of non-destructive ultrasonic frequencies. The method may further comprise selecting a frequency from within the range of 10 kHz to 1 MHz.

The method may further comprise selecting a frequency of the sound waves for transmission through the sample, where the wavelength corresponding to the frequency selected is a predetermined ratio relative to an average diameter of the particles constituting the sample so as to substantially minimise scattering losses. It should be appreciated that the determination of the average diameter of the particles constituting the sample need only be a crude measurement. This measurement is a one off measurement and need not be repeated for measurements performed on the same material. The wavelength of the sound waves is preferably at least 10 times the average diameter of the particles, more preferable at least 20 times the average diameter of the particles, and still more preferably at least 25 times the average diameter of the particles.

In one embodiment, the method may include removing a sample of material for testing. In this embodiment, the method may involve placing the sample in a container, applying a pressure to the sample in the container to an extent necessary to pressurise the sample to facilitate sound transmission through the sample. In this embodiment, the selected criteria may be the pressure applied to the article and the bulk density of the sample. From a knowledge of the volume of the container and the mass of the sample, it is a simple procedure to determine the bulk density of the sample.

According to a second aspect of the invention, there is provided a system for determining average properties of constituent particles of a sample of material, the system including:

a sound generating unit for generating sound waves of a predetermined frequency to be transmitted through the sample;

a receiver for receiving a signal representative of sound waves transmitted through the sample;

a reference unit for providing reference data regarding selected criteria associated with the sample; and a signal processing unit for processing the received signal and, using the data from the reference unit, determining, independently of particle size of particles constituting the sample average properties of the particles constituting the sample.

The sound waves to be transmitted through the sample may be selected to have a wavelength which is a predetermined ratio relative to an average diameter of the particles constituting the sample to avoid scattering losses. Preferably, the wavelength of the sound waves is at least 10 times the average diameter of the particles, and more particularly greater than about 20 times the average diameter of the particles, and still more preferably greater than about 25 times the average diameter of the particles The sound waves to be transmitted through the sample may be selected to have a frequency within the range of non-destructive ultrasonic frequencies. The sound waves to be transmitted through the sample may be selected to have a frequency within the range of 10 kHz to 1 MHz.

The sound waves transmitted through the sample may be shear waves or may be longitudinal waves.

The sound generating unit may include a transducer to transmit the sound waves through the sample and a sound generator to drive the transducer at the predetermined frequency. The sound generator may be a pulse generator.

In one embodiment, the receiver may comprise a separate transducer. In an optional embodiment, the transducer which transmits the sound waves through the sample may function as the receiver. In such an embodiment the system may further include a reflective surface arranged to reflect sounds waves transmitted through the sample back to the transducer.

It should be appreciated that the invention is not limited to the arrangement of the transducer(s) as this will depend on the number of transducers and the type of sound wave generated.

The selected criteria associated with the sample may include a bulk density, a specific gravity and Poisson's Ratio of the sample of material.

The signal processing unit may comprise an analyser which analyses the received signal to determine the required properties of the sample. The analyser may include, or communicate with, the reference unit.

The average properties to be determined may include hardness or strength of the particles constituting the sample. The particle strength or hardness may be used to determine other physical properties such as, for example, dusting characteristics.

The signal processing unit may include an oscilloscope for displaying the transmitted sound wave. The sound generating unit may simultaneously trigger an oscilloscope trace and the pulse generator.

The system may further comprise a pressure means to apply pressure to the sample to facilitate transmission of the sound wave through the sample of material. The pressure means may comprise an adjustable pressure plate, or the like.

The system may further comprising a pressure sensor in communication with the reference unit to sense a pressure applied to the sample.

An embodiment of the system may be provided for determining average properties of constituent particles of a sample of material in-situ. For instance material sampled from a continuous stream of an aggregate, such as a stream of pellets, may be tested with the material being thereafter returned to the stream. In this embodiment of the invention, the reference unit may use a bulk density measuring device to determine the bulk density of the sample. The density measuring device may comprise a gamma-ray density gauge, or the like. To obtain data relating to the pressurising of the sample, the sample may be diverted from the continuous stream to a hopper, or the like, with a mass of a column of the material on the hopper generating the required pressure.

The hopper may have a pressure cell, or sensor, on its floor. The sample, once tested, may be discharged from the hopper and fed back into the stream.

In accordance with the invention a system is provided, the use of which enables the relatively rapid determination of average properties of a bulk material through a non destructive technique. The system facilitates the measurement of sound waves through a sample of material, enables the ultrasonic velocity to be measured with accuracy, even in the case of non-spherical particles whose degree of non-sphericality lies within a normal standard deviation, enables calculation of the Young's modulus of the particles, and therefore enables the calculation of the hardness, or strength, of particles in a sample of material. Furthermore, operation of the system on-line enables operators of the system to receive information relatively quickly such that changes can be made to ensure that the quality of the material meets the required standard.

DETAILED DESCRIPTION OF EXEMPLARY EMBODIMENTS

Figure 1:
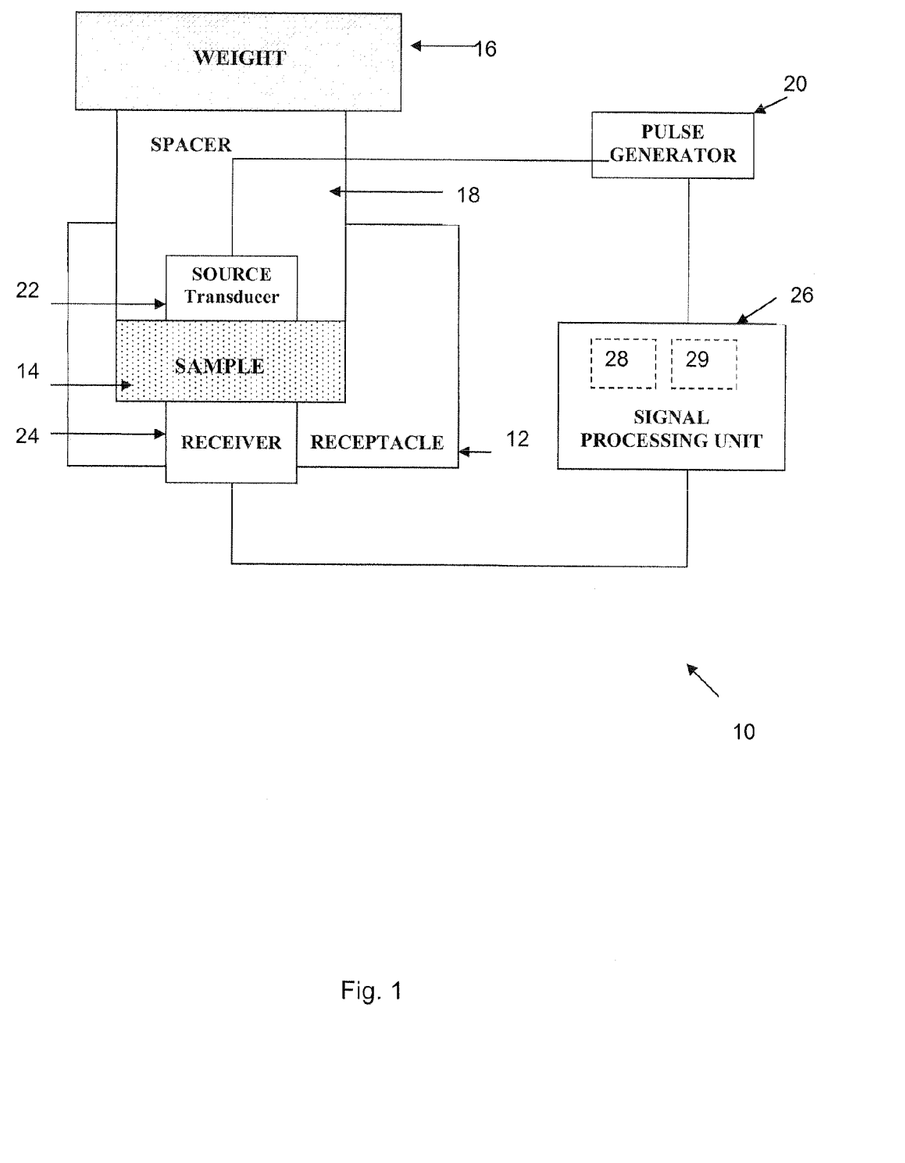
FIG. 1 shows a schematic block diagram of an experimental setup of a system, in accordance with an embodiment of the invention, for determining average properties of constituent particles of a sample of material.

In FIG. 1 of the drawings, reference numeral 10 generally designates an experimental setup of a system, in accordance with an embodiment of the invention for determining average properties of constituent particles of a sample of material.

The system 10 includes a receptacle 12 in which a sample of material 14 to be tested is received. A pressurising device in the form of a weight 16 is applied to a top surface of the sample of material 14 via a spacer 18.

The system includes a sound generating unit in the form of a pulse generator 20 and a source transducer 22. The pulse generator 20 generates a signal at a predetermined frequency and amplitude and stimulates the source transducer 22 to convert the signal into a sound wave at the appropriate frequency for propagation through the sample of material 14. The system further includes a receiver in the form of a transducer 24 which monitors the arrival of sound waves that have passed through the sample of material 14 and in response generates a signal.

A pressure sensor (not shown) is provided to sense the pressure applied to the sample of material 14.

The system 10 further includes a signal processing unit 26 for processing the received sound signal generated by the transducer 24. The signal processing unit 26 includes circuitry (not shown) to amplify and filter the signal and further includes an oscilloscope 29 for displaying the signal generated by the pulse generator 20.

Incorporated into the system 10 is a reference unit 28 which provides reference data regarding selected criteria associated with the sample of material 14. In the embodiment of the invention illustrated in FIG. 1 of the drawings, the reference data 28 includes data output from the pressure sensor, the specific gravity, Poisson's Ratio of the particles constituting the sample of material 14 and the bulk density of the sample of material 14 which is calculated due to the known volume of the sample of material 14 and the mass of the sample of material 14.

In determining the strength of particles constituting the sample of material 14, a sound wave, having a velocity V, injected into the sample of material 14 is attenuated. The speed of the wave through the sample of material 14 depends on two factors: the density, ρ, of the sample of material 14 and the elastic modulus, E, of the particles constituting the sample of material 1 (referred to as the Young's modulus). The Young's modulus provides an indication of the "strength" or "resilience" of the particles constituting the sample material 14 however this parameter can be difficult to measure and interpret where the sample of material 14 is constituted by groups of loose particles.

Much of the physics of sound transmission in granular solids can be understood in terms of contact between spheres. In a loose aggregate there is essentially no transmission of sound waves through the particles as there is no resistance to small displacements of the particles. Pressure is required to make solid contact between the particles constituting the sample of material 14 to facilitate sound transmission.

The physics of sound transmission in granular solids, where the particles are randomly packed, can be found in the paper "*The Effective Elastic Moduli of Porous Granula Rocks*", Digby P. J., Journal of Applied Mechanics, December 1981 Vol 48, pages 803 to 808, the disclosure of which is incorporated herein for reference. The sound velocity as a function of the Young's Modulus can be thus derived:

$$V = 0.392 V_b \left( K^{1/3} \left( \frac{1}{1-v} \right)^{1/3} \left( \frac{1}{1-\alpha} \right)^{1/6} \left( \frac{P}{E} \right)^{1/6} \right)$$

where:
V is the sound velocity of the wave injected into the sample of material 14,
$V_b$ is the sound velocity of the sound wave transmitted through the sample of material 14,
K is the average number of contacts for each sphere, which for a random packing is 8.84,
α is the voidage fraction (porosity),
v is Poisson's ratio of the individual particles in the sample of material 14,
P is the applied pressure, and
E is the Young's modulus of the particles constituting the sample of material 14.

It will be noted, firstly, from this equation that the sound velocity is proportional to 0.167 the power of the pressure applied by the weight 16.

In deriving the above equation it is assumed that the interparticle stickiness is zero. Furthermore, the principal assumption made is that the wavelength of the sound wave transmitted through the sample of material 14 is substantially greater than the average particle size. The particle size should be unimportant to loss until scattering becomes an important effect, i.e. when the particle size becomes comparable to the wavelength of the sound wave. In the case of spherical materials, high losses are associated with a ratio of wavelength to particle diameter of about ten or less. The ratio of wavelength to the average particle diameter for any application should, therefore, be at least twenty and, preferably, of the order of twenty five.

Reverting to the above equation, it follows that to calculate the Young's Modulus, and hence the average particle strength, it is necessary to know, the bulk density of the sample of material 14, the specific gravity and Poisson's Ratio of the particles constituting the sample of material 14. As will be noted there is essentially no dependence on particle size in the sound velocity. Measurements of the sound velocity of the sound wave transmitted through the sample of material 14, together with a measurement of the pressure applied to the sample enable a determination of the Young's Modulus.

The signal processing unit 26 may contain appropriate electronics to take into consideration transmission losses. Transmission losses occurring in the measurement of acoustic signals have two sources, the first being intrinsic attenuation where the material of the sample 14 causes the sound wave to lose amplitude during transmission. The second source arises from insertion losses due to the difficulty of transmitting the sound wave between the sample of material 14 and the transducers 22, 24.

In some embodiments coupling gels may be added to the sample of material to maximise the effective coupling area. Such a measure ensures that the surface roughness of individual particles does not lead to poor sound transmission.

In testing the system 10, materials tested were principally glass impact media of grades AH, AE, AD and AC. These materials have relatively narrow particle size distributions and mean particle diameters of 50, 106, 157 and 165 microns respectively. 100G Silica Flour was also used which is essentially the same material as glass impact media but with a broad size distribution about 20 microns in diameter with an extreme, plate like, non-spherical shape. Iron ore and coal powders were used as examples of industrial material with particle sizes of approximately 50 microns in mean diameter, such powders are also non-spherical having a generally cubic shape.

The transducers 22, 24 were approximately 25 mm in diameter. The sample of material which formed a column had a diameter of about 70 mm. Each sample of material weighed approximately 130 grams and had a height of the order of a few hundred millimeters. Various weights 16 were applied to adjust the pressure applied to the sample of material 14.

Figure 2:
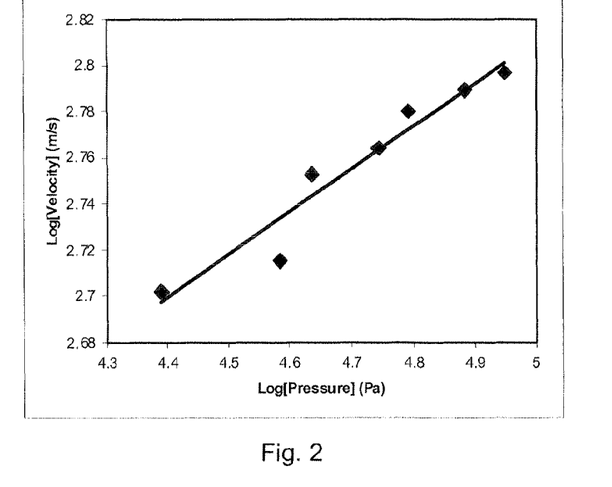
FIG. 2 shows a plot of ultrasonic velocity against pressure for glass impact media used in the system of FIG. 1.

In FIG. 2 of the drawings, a plot of the logarithm of velocity of the sound wave against the logarithm of pressure in the sample of material 14 of grade AH glass impact media is shown.

The velocity of the sound wave was measured by timing the delay from the trigger associated with the ultrasonic pulse generated by the pulse generator 20 to the first zero crossing of the received wave form by the signal processing unit 26. A value obtained with no glass impact media present was used to calibrate out the delays inherent in the system 10.

The slope of the plot in FIG. 2 is 0.184 including all measured points and 0.171 excluding the anomalous point for the second lowest pressure. This agrees closely with the predicted value of 0.167. Table 1 below shows the measured and predicted velocities from the equation above for various sizes of glass impact media and the other materials at a maximum pressure of 88.8 kPa. It will be noted from the table below that the absolute value of measured velocity is surprisingly close to the predicted levels even for the materials comprising markedly non-spherical particles. The one exception to this is the silica flour which is the finest and most extreme of the non-spherical of the particles. The most likely explanation for an error in this case is incorrect material properties used in the calculation and the extreme non-spherical nature of the particles.

TABLE 1

Sound Velocity Measurements

| Material | Spherical (Yes/No) | Measured Speed (ms$^{-1}$) | Predicted Speed (ms$^{-1}$) |
|---|---|---|---|
| AH | Yes | 626 | 649 |
| AE | Yes | 681 | 671 |
| AD | Yes | 522 | 638 |
| AC | Yes | No Signal | |
| 100G Si Flour | No | 275 | 628 |
| Coal Dust | No | 357 | 324 |
| Iron Ore | No | 251 | 244 |

It is to be noted that the ratio of applied pressure to Young's modulus for the sample of material is of the order of $10^{-6}$. With pressures this small, permanent deformation or damage to the particles constituting the sample of material 14 is unlikely which should enable accurate, repeatable measurements to be obtained.

A sample of material 14 of grade AH glass impact media was used to investigate the relationship of insertion loss and intrinsic loss to pressure as it was the material which provided the most reliable measurements. The amplitude of the pulse was measured at a fixed pressure for a range of sample thicknesses. On the assumption that the insertion loses and intrinsic losses are constant for a given pressure these measurements allow the insertion loss to be determined by extrapolating the total loss to zero bed thickness. The intrinsic loss can also be determined by fitting a slope to the total loss at different bed thicknesses. The measurements were repeated for a range of pressures.

For a variety of pressures in grade AH glass impact media, the total loss in dB was approximately linear with bed depth allowing for sensible measurements of both losses.

As indicated above, particle size is unimportant to loss until scattering becomes an important effect, i.e. when the particle size becomes comparable to the wavelength of the ultrasonic sound signal. The wavelength is determined by the ratio of the measured velocity and the signal frequency.

For spherical material it appears that high losses are associated with a ratio of 10 or less and, as indicated above, the ratio of wavelength to particle diameter for any application should be of the order of 25. With this wavelength to particle diameter ratio, estimates of loss for other material that could be useful in an industrial context can be performed.

Figure 3:
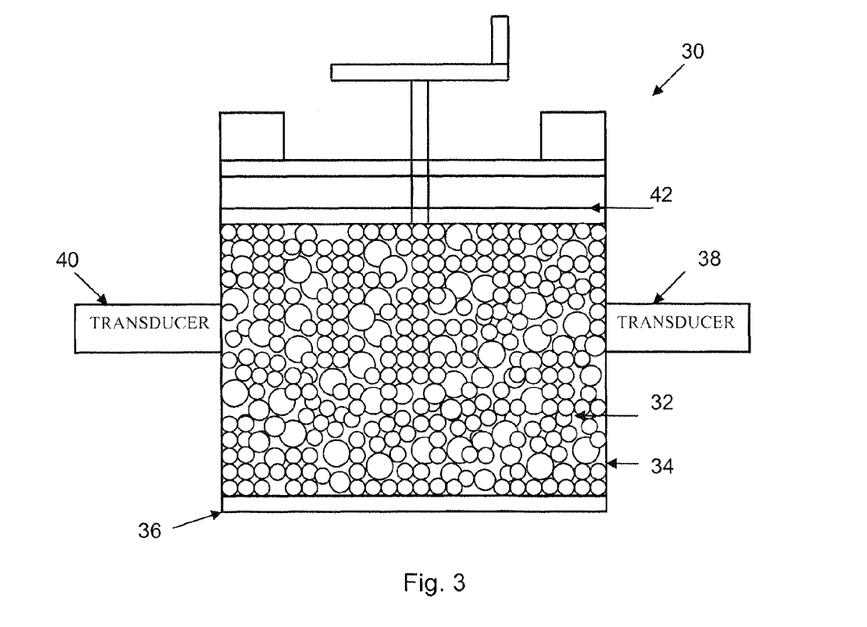
FIG. 3 shows a schematic block diagram of a bench top system in accordance with the invention.

Referring now to FIG. 3 of the drawings, a bench top system 30 for determining average properties of a sample of material is illustrated. In this application, a sample of material 32 is removed as a batch and placed in a receptacle 34. A pressure cell 36 is mounted on a floor of the receptacle 34 and transducers 38 and 40 are applied to sidewalls of the receptacle 34 in an opposed relationship. Pressure is applied via an adjustable pressure plate 42 to the sample of material 32.

In this implementation, an ultrasonic sound signal is generated and converted into a sound wave via the transducer 38 and transmitted through the sample of material. The sound waves that have passed through the sample of material are measured by the transducer 40 and passed to a signal processing unit (not shown in this Figure but substantially the same as the unit 26 in FIG. 1 of the drawings). Because the volume of the receptacle 34 is known the bulk density can be determined from the measurement obtained from the pressure cell 36.

Using the equation above, for a random packed sample of material 32, the particle strength of the sample of material 32 can be determined from the measured velocity of the sound signal through the sample of material 32.

Figure 4:
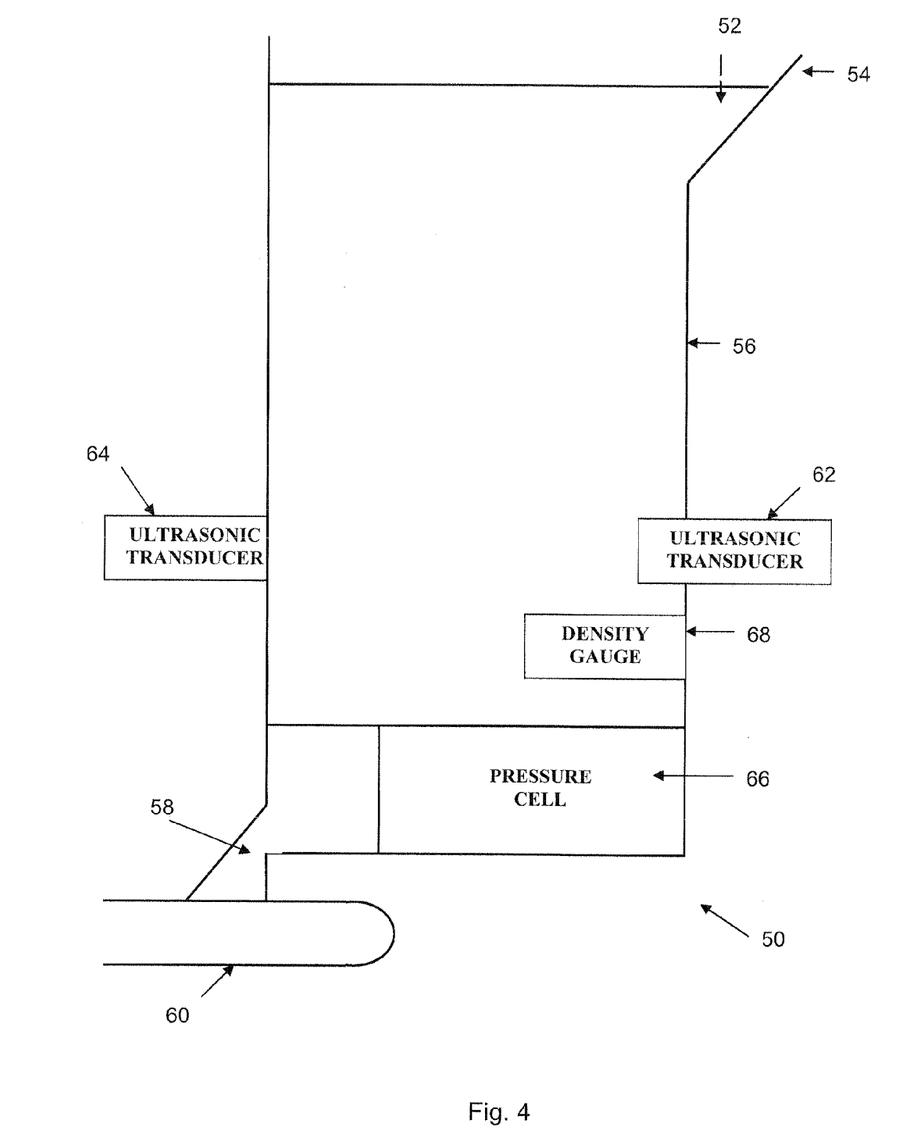
FIG. 4 shows a schematic block diagram of an in-situ system in accordance with the invention.

In FIG. 4 of the drawings, main components of an in-situ system 50 are shown. In this embodiment of the invention, a sample of fluent material 52 is diverted from a production line into an opening 54 of a hopper 56. The hopper 56 has a discharge opening 58 for discharging the sample on to the feed 60 for return to the production line. Ultrasonic transducers 62 and 64 are arranged in diametrically opposed relationship on a wall of the hopper 56. A pressure cell 66 is mounted on a floor of the hopper 56.

Because this is a flow through application, a further measurement of bulk density is required by a suitable bulk density measuring device such as a gamma-ray density gauge 68.

Further, in the case of the flow through application, the pressure applied to the pressure cells 66 is produced by the mass of the material above the pressure cell 66 and, consequently, is a function of the depth of the hopper 56.

Hence, by means of the invention, a system 10 is provided which enables the relatively rapid determination of properties of particles making up powders and aggregates through a non destructive technique. The system facilitates the measurement of sound waves through a sample of material, enables the ultrasonic velocity to be measured with accuracy, even in the case of non-spherical particles whose degree of non-sphericality lies within a normal standard deviation, enables calculation of the Young's modulus of the particles, and from the Young's modulus enables the calculation of the hardness, or strength, of particles in a sample of material. Furthermore, operation of the system on-line enables operators of the system to receive information relatively quickly such that changes can be made to ensure that the quality of the material meets the required standard.

It will be appreciated that one or more of these advantages are extremely advantageous in certain industries such as the iron ore or alumina industries.

As known in the iron ore industry, briquettes of fine powders are destructively tested to assess the integrity of the briquettes. Often, this occurs only after the briquettes have been fired and, if briquettes of inadequate strength are being formed, the production line needs to be re-set. Advantageously, the present invention can be used on green, or pre-fired, briquettes resulting in the ability to take remedial action more rapidly.

Likewise, in the case of the alumina industry, major problems occur with dusting of the alumina powder. It is beneficial to be able to reduce this dusting as much as possible as dusting can cause clogging which could have serious consequences. Once again, by use of the system 10, non-destructive testing of alumina powder samples can be performed. This again facilitates the ability to take remedial action in the event of unsatisfactory alumina powder samples.

Figure 5:
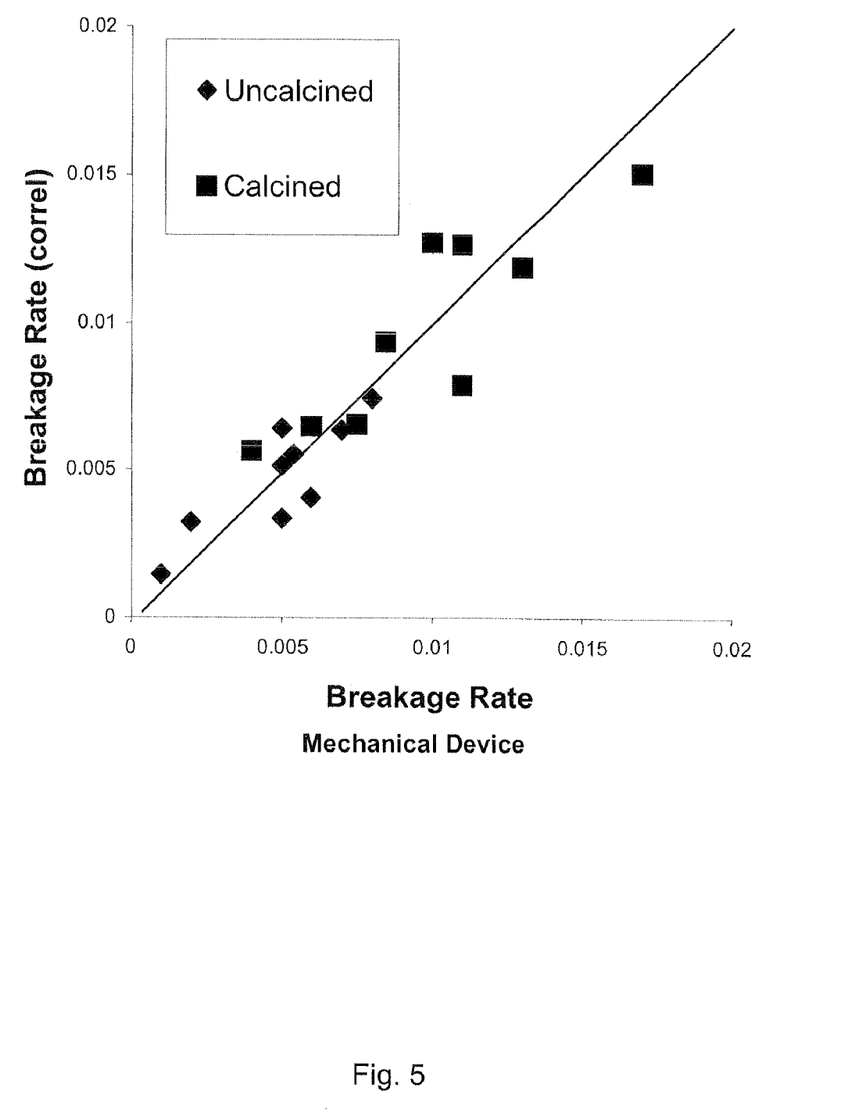
FIG. 5 shows a plot of the correlation between the breakage rate of calcined and uncalcined alumina obtained via an apparatus as shown in FIG. 1, with the breakage rate for calcined and uncalcined alumina obtained via a traditional apparatus.

Samples of calcined and uncalcined alumina were measured for dusting characteristics using the apparatus as described above in relation to FIG. 1. These calcined and uncalcined alumina samples were also measured for their dusting characteristics in a separate traditional mechanical shaking device. In the traditional shaking device, the size of individual particles were measured before and after intervals of shaking. From the measurement of particle size, the particle strength and hence breakage rate was determined. The mechanical breakage rate was measured and correlated with the breakage rate obtained from the measured velocity using the apparatus as described in relation to FIG. 1. Good correlation rates, as illustrated in FIG. 5, were obtained.

Figure 6:
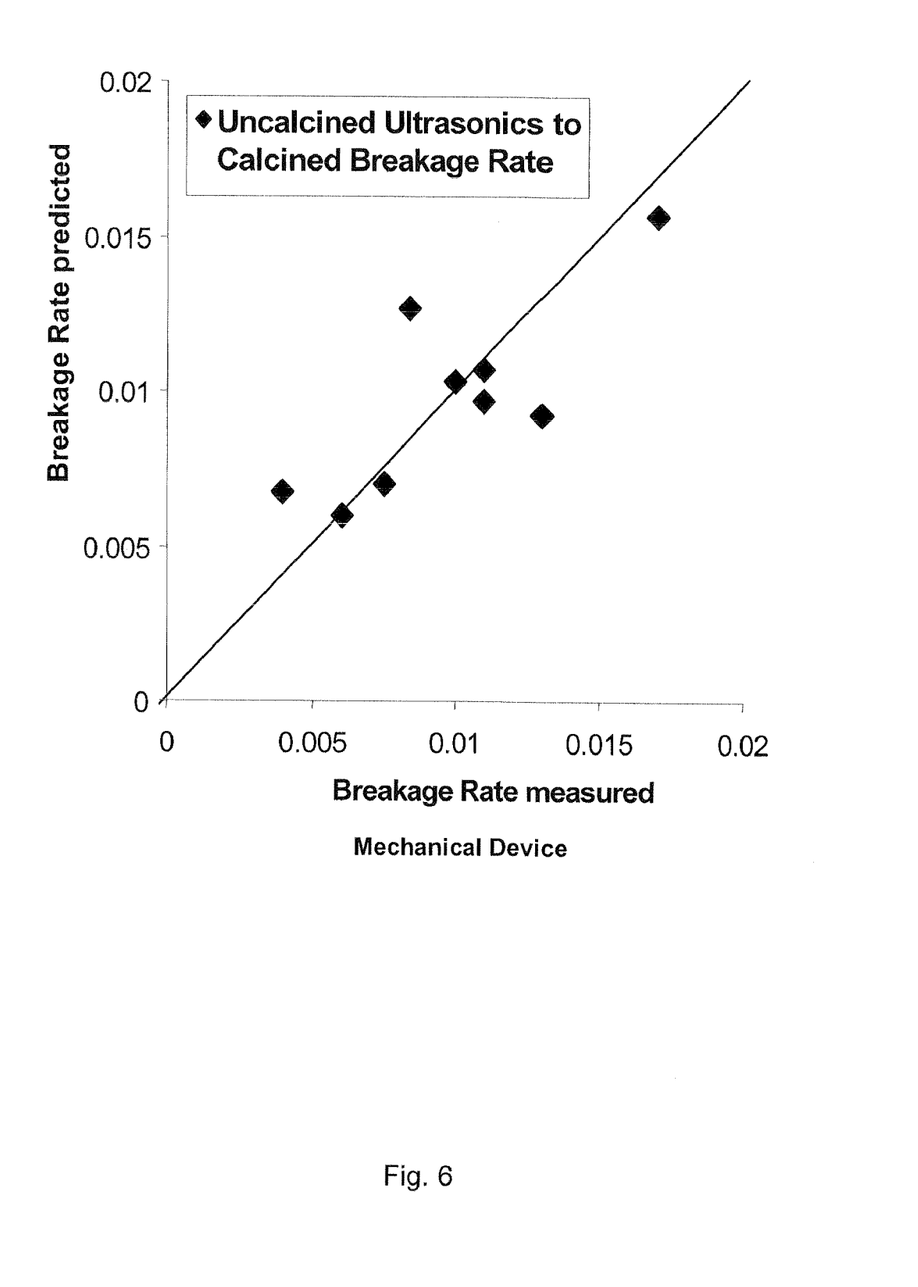
FIG. 6 shows a plot of the correlation between the breakage rate of uncalcined alumina obtained via an apparatus as shown in FIG. 1, with the breakage rate with calcined alumina obtained via a traditional apparatus.

FIG. 6 illustrates the correlation of the breakage rate of the uncalcined data (obtained with the apparatus in accordance with the invention) with the breakage rate of the calcined data (obtained with the traditional equipment). Again a reasonable correlation of R=0.8 is illustrated. These results demonstrate the viability of the apparatus to test dusting characteristics of the alumina powder. This results in improvements in the alumina industry as the test can be performed on uncalcined alumina which is much easier to recycle than calcined alumina.

Other applications of the system 10 are in the powder detergent industry where problems with product strength also occur.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A system for determining average properties of constituent particles of a sample of material, the system comprising:
    a sound generating unit for generating sound waves of a predetermined frequency to be transmitted through the sample;
    a receiver for receiving a signal representative of sound waves transmitted through the sample;
    a reference unit for providing reference data regarding selected criteria associated with the sample; and
    a signal processing unit for processing the received signal to determine the sound velocity of sound waves transmitted through the sample and, using the data from the reference unit, determining, independently of particle size of particles constituting the sample the Young's modulus of the constituent particles based on the measured sound velocity, and average properties of the particles constituting the sample.

2. A system according to claim 1, where the sound waves to be transmitted through the sample are selected to have a wavelength which is a predetermined ratio relative to an average diameter of the particles constituting the sample so as to substantially minimize scattering losses.

3. A system according to claim 2, where the wavelength of the sound waves is at least 10 times the average diameter of the particles.

4. A system according to claim 3, where the wavelength of the sound waves is at least 20 times the average diameter of the particles.

5. A system according to claim 4, where the wavelength of the sound waves is at least 25 times the average diameter of the particles.

6. A system according to claim 1, where the sound waves to be transmitted through the sample are selected to have a frequency within a range of non-destructive ultrasonic frequencies.

7. A system according to claim 6, where the sound waves transmitted through the sample are selected to have a frequency within the range of 10 kHz to 1 MHz.

8. A system according to claim 1, where the sound waves to be transmitted through the sample are shear waves.

9. A system according to claim 1, where the sound waves to be transmitted through the sample are longitudinal waves.

10. A system according to claim 1, where the sound generating unit comprises a transmitting transducer to transmit the sound waves through the sample and a sound generator to drive the transducer at the predetermined frequency.

11. A system according to claim 10, where the sound generator is a pulse generator.

12. A system according to claim 10, where the receiver comprises a receiving transducer.

13. A system according to claim 1, further comprising a device to applying pressure to the sample to facilitate transmission of the sound wave through the sample of material.

14. A system according to claim 1, further comprising a pressure sensor in communication with the reference unit to sense a pressure applied to the sample.

15. A system according claim 1, where the selected criteria associated with the sample includes a bulk density, a specific gravity and Poisson's Ratio of the particles constituting the sample of material.

16. A system according to claim 1, where the signal processing unit comprises an analyzer which analyses the received sound signal to determine the average properties of the particles constituting the sample.

17. A system according to claim 1, where an average property of the particles constituting the sample is the average strength of particles constituting the sample.

18. A system according to claim 1, where the system is an in-situ system for measuring a sample of material in-situ, the system further comprising a hopper to hold a diverted sample of material to be tested and the reference unit uses a density measuring device to determine the bulk density of the sample.

19. A system according to claim 18, where the density measuring device is a gamma-ray density gauge.

20. A system according to claim 18, further comprising a pressure sensor mounted in a floor of the hopper.

21. A method for determining average properties of constituent particles of a sample of material, the method comprising:
    transmitting sound waves of a predetermined frequency through the sample;

receiving a sound signal representative of sound waves transmitted through the sample;

providing reference data regarding selected criteria associated with the sample; and processing the received signal to determine the sound velocity of sound waves transmitted through the sample and using the reference data to determine, independently of particle size of particles constituting the sample, the Young's modulus of the constituent particles based on the measured sound velocity, and predetermined average properties of the particles constituting the sample.

22. A method according to claim 21, where the Young's modulus of the particles is obtained from an equation derived from a random packing order of spheres:

$$V = 0.392 V_b \left( K^{1/3} \left( \frac{1}{1-\nu} \right)^{1/3} \left( \frac{1}{1-\alpha} \right)^{1/6} \left( \frac{P}{E} \right)^{1/6} \right)$$

where: V is the sound velocity of the wave injected into the sample of material, $V_b$ is the sound velocity of the sound wave transmitted through the sample of material, K is the average number of contacts for each sphere, α is the voidage fraction, ν is Poisson's ratio of the individual particles in the sample of material, P is the applied pressure, and E is the Young's modulus.

23. A method according to claim 22, where determining an average property of the particles constituting the sample comprises calculating an average strength of the particles.

24. A method according to claim 23, further comprising applying a pressure to the sample to facilitate sound transmission through the sample.

25. A method according to claim 24, where the pressure applied to the sample is of the order of $10^{-6}$ of the Young's modulus of particles of the sample.

26. A method according to claim 21, further comprising measuring a pressure applied to the sample.

27. A method according to claim 21, further comprising measuring a bulk density of the sample of material.

28. A method according to claim 21, further comprising selecting a frequency of the sound waves for transmission through the sample, where the wavelength corresponding to the frequency selected is a predetermined ratio relative to an average diameter of the particles constituting the sample so as to substantially minimize scattering losses.

29. A method according to claim 28, where the wavelength of the sound waves is at least 10 times the average diameter of the particles.

30. A method according to claim 29, where the wavelength of the sound waves is at least 20 times the average diameter of the particles.

31. A method according to claim 30, where the wavelength of the sound waves is at least 25 times the average diameter of the particles.

32. A method according to claim 21, further comprising selecting a frequency of the sound waves for transmission through the sample, where the frequencies are selected within a range of non-destructive ultrasonic frequencies.

33. A method according to claim 32, further comprising selecting a frequency from within the range of 10 kHz to 1 MHz.

* * * * *